United States Patent [19]

Craig et al.

[11] Patent Number: 5,763,276
[45] Date of Patent: Jun. 9, 1998

[54] PROCESSES FOR THE PURIFICATION OF HUMAN RECOMBINANT DECORIN AND THE DETECTION OF GUANDINIUM IONS

[75] Inventors: William S. Craig; John R. Harper, both of San Diego; Sam D. Hernandez, Carlsbad; Paul J. Kostel, San Diego; Jonathan R. Parker, Jamul; Thomas S. Vedvick, Carlsbad, all of Calif.

[73] Assignee: La Jolla Cancer Research Foundation, La Jolla, Calif.

[21] Appl. No.: 619,916

[22] Filed: Mar. 20, 1996

Related U.S. Application Data

[62] Division of Ser. No. 272,919, Jul. 8, 1994, Pat. No. 5,567,807.

[51] Int. Cl.$^6$ .......................... G01N 33/00; G01N 27/00; C07K 1/20
[52] U.S. Cl. .............................. 436/111; 435/4; 436/149; 530/395
[58] Field of Search ......................... 435/4; 436/111, 436/149; 530/395, 416

[56] References Cited

FOREIGN PATENT DOCUMENTS

WO 90/00194  1/1990  WIPO.

OTHER PUBLICATIONS

Krusius and Ruoslahti, "Primary structure of an extracellular matrix proteoglycan core protein deduced from cloned cDNA." *Proc. Natl. Acad. Sci. USA*, 83:7683–7687 (1986).

Ruoslahti, Erkki, "structure and biology of proteoglycene." *Ann. Rev. Cell Biol.*, 4:229–255 (1988).

Choi et al., "Characterization of the dermatan sulfate proteoglycans, DS-PGI and DS-PGII, from bovine articular cartilage and skin isolated by octyl-sepharose chromatography." *J. of Biol. Chem.*, 264(5):2876–2884 (1989).

*Primary Examiner*—Ponnathapura Achutamurthy
*Attorney, Agent, or Firm*—Campbell & Flores LLP

[57] ABSTRACT

The invention provides a process for detecting the presence of guanidinium ions in a sample solution. The detection process involves contacting a sample solution suspected of containing guanidinium ions with a cation exchange resin and eluting the guanidinium ions present in the sample solution with an aqueous buffer solution having a pH of about 1.5 to about 2. This is followed by contacting the eluant with a cation suppressor column and simultaneously flowing a suppressor regenerate solution in the opposite direction on the opposite side of the permeable membrane of the column, and finally, detecting the presence of guanidinium ions in the eluant from the ion exchange column which was contacted with the suppressor column by use of a conductivity detector.

6 Claims, 5 Drawing Sheets

Anti-CHO

Anti-Decorin

```
        130              140            150            160             170
          |               |              |              |               |
---    GGA CCG TTT CAA CAG AGA GGC TTA TTT GAC TTT ATG CTA GAA
---    Gly Pro Phe Gln Gln Arg Gly Leu Phe Asp Phe Met Leu Glu
        |                        |
       -13                      -10

180            190            200             210
           |              |              |               |
GAT GAG GCT TCT GGG ATA GGC CCA GAA GTT CCT GAT GAC CGC GAC
Asp Glu Ala Ser Gly Ile Gly Pro Glu Val Pro Asp Asp Arg Asp
 |                                     |
 1                                    10

220            230            240             250            260
         |              |              |               |              |
TTC GAG CCC TCC CTA GGC CCA GTG TGC CCC TTC CGC TGT CAA TGC
Phe Glu Pro Ser Leu Gly Pro Val Cys Pro Phe Arg Cys Gln Cys
                             |                                        |
                            20                                       30

270            280            290            300
         |              |              |              |
CAT CTT CGA GTG GTC CAG TGT TCT GAT TTG GGT CTG GAC AAA GTG
His Leu Arg Val Val Gln Cys Ser Asp Leu Gly Leu Asp Lys Val
                                         |
                                        40

310            320            330            340            350
         |              |              |              |              |
CCA AAG GAT CTT CCC CCT GAC ACA ACT CTG CTA GAC CTG CAA AAC
Pro Lys Asp Leu Pro Pro Asp Thr Thr Leu Leu Asp Leu Gln Asn
                         |                                            |
                        50                                           60

360            370            380            390
           |              |              |              |
AAC AAA ATA ACC GAA ATC AAA GAT GGA GAC TTT AAG AAC CTG AAG
Asn Lys Ile Thr Glu Ile Lys Asp Gly Asp Phe Lys Asn Leu Lys
                                         |
                                        70
```

FIG. 1A

```
        400              410              420              430              440
         |                |                |                |                |
AAC CTT CAC GCA TTG ATT CTT GTC AAC AAT AAA ATT AGC AAA GTT
Asn Leu His Ala Leu Ile Leu Val Asn Asn Lys Ile Ser Lys Val
                        |                                   |
                        80                                  90

450              460              470              480
             |                |                |                |
AGT CCT GGA GCA TTT ACA CCT TTG GTG AAG TTG GAA CGA CTT TAT
Ser Pro Gly Ala Phe Thr Pro Leu Val Lys Leu Glu Arg Leu Tyr
                                        |
                                       100

490              500              510              520              530
         |                |                |                |                |
CTG TCC AAG AAT CAG CTG AAG GAA TTG CCA GAA AAA ATG CCC AAA
Leu Ser Lys Asn Gln Leu Lys Glu Leu Pro Glu Lys Met Pro Lys
                                |                                   |
                               110                                 120

540              550              560              570
             |                |                |                |
ACT CTT CAG GAG CTG CGT GCC CAT GAG AAT GAG ATC ACC AAA GTG
Thr Leu Gln Glu Leu Arg Ala His Glu Asn Glu Ile Thr Lys Val
                                        |
                                       130

580              590              600              610              620
             |                |                |                |                |
CGA AAA GTT ACT TTC AAT GGA CTG AAC CAG ATG ATT GTC ATA GAA
Arg Lys Val Thr Phe Asn Gly Leu Asn Gln Met Ile Val Ile Glu
                                |                                   |
                               140                                 150

630              640              650              660
                 |                |                |                |
CTG GGC ACC AAT CCG CTG AAG AGC TCA GGA ATT GAA AAT GGG GCT
Leu Gly Thr Asn Pro Leu Lys Ser Ser Gly Ile Glu Asn Gly Ala
                                        |
                                       160
```

FIG. 1B

```
     670           680           690           700           710
      |             |             |             |             |
TTC CAG GGA ATG AAG AAG CTC TCC TAC ATC CGC ATT GCT GAT ACC
Phe Gln Gly Met Lys Lys Leu Ser Tyr Ile Arg Ile Ala Asp Thr
                 |                                         |
                170                                       180

720           730           740           750
      |             |             |             |
AAT ATC ACC AGC ATT CCT CAA GGT CTT CCT CCT TCC CTT ACG GAA
Asn Ile Thr Ser Ile Pro Gln Gly Leu Pro Pro Ser Leu Thr Glu
                                     |
                                   190

760           770           780           790           800
      |             |             |             |             |
TTA CAT CTT GAT GGC AAC AAA ATC AGC AGA GTT GAT GCA GCT AGC
Leu His Leu Asp Gly Asn Lys Ile Ser Arg Val Asp Ala Ala Ser
                       |                                   |
                      200                                 210

810           820           830           840
      |             |             |             |
CTG AAA GGA CTG AAT AAT TTG GCT AAG TTG GGA TTG AGT TTC AAC
Leu Lys Gly Leu Asn Asn Leu Ala Lys Leu Gly Leu Ser Phe Asn
                                     |
                                   220

850           860           870           880           890
      |             |             |             |             |
AGC ATC TCT GCT GTT GAC AAT GGC TCT CTG GCC AAC ACG CCT CAT
Ser Ile Ser Ala Val Asp Asn Gly Ser Leu Ala Asn Thr Pro His
                             |                             |
                           230                            240

900           910           920           930
      |             |             |             |
CTG AGG GAG CTT CAC TTG GAC AAC AAC AAG CTT ACC AGA GTA CCT
Leu Arg Glu Leu His Leu Asp Asn Asn Lys Leu Thr Arg Val Pro
                                     |
                                   250
```

FIG. 1C

```
        940              950              960              970              980
         |                |                |                |                |
GGT GGG CTG GCA GAG CAT AAG TAC ATC CAG GTT GTC TAC CTT CAT
Gly Gly Leu Ala Glu His Lys Tyr Ile Gln Val Val Tyr Leu His
                         |                                          |
                        260                                        270

990             1000             1010             1020
              |                |                |                |
AAC AAC AAT ATC TCT GTA GTT GGA TCA AGT GAC TTC TGC CCA CCT
Asn Asn Asn Ile Ser Val Val Gly Ser Ser Asp Phe Cys Pro Pro
                                     |
                                    280

1030             1040             1050             1060             1070
         |                |                |                |                |
GGA CAC AAC ACC AAA AAG GCT TCT TAT TCG GGT GTG AGT CTT TTC
Gly His Asn Thr Lys Lys Ala Ser Tyr Ser Gly Val Ser Leu Phe
                         |                                          |
                        290                                        300

1080             1090             1100             1110
              |                |                |                |
AGC AAC CCG GTC CAG TAC TGG GAG ATA CAG CCA TCC ACC TTC AGA
Ser Asn Pro Val Gln Tyr Trp Glu Ile Gln Pro Ser Thr Phe Arg
                                     |
                                    310

1120             1130             1140             1150
              |                |                |                |
TGT GTC TAC GTG CGC TCT GCC ATT CAA CTC GGA AAC TAT ---
Cys Val Tyr Val Arg Ser Ala Ile Gln Leu Gly Asn Tyr ---
                    |
                   320
```

FIG. 1D

PROCESSES FOR THE PURIFICATION OF HUMAN RECOMBINANT DECORIN AND THE DETECTION OF GUANDINIUM IONS

This application is a divisional of application Ser. No. 02/272,919, filed Jul. 8, 1994, now issued as U.S. Pat. No. 5,567,807.

BACKGROUND OF THE INVENTION

FIELD OF THE INVENTION

This invention relates generally to processes of purifying proteins and detecting residual ions in protein-containing, or other, solutions.

Decorin, also known as PG-II or PG-40, is a small proteoglycan produced by fibroblasts. Its core protein has a molecular weight of about 40,000 daltons. The core has been sequenced and it is known to carry a single glycosaminoglycan chain of the chondroitin sulfate/dermatan sulfate type. Most of the core protein of decorin is characterized by the presence of a leucine-rich repeat (LRR) of about 24 amino acids.

Proteoglycans are proteins that carry one or more glycosaminoglycan chains. The known proteoglycans carry out a wide variety of functions and are found in a variety of cellular locations. Many proteoglycans are components of extracellular matrix, where they participate in the assembly of matrix and effect the attachment of cells to the matrix.

Decorin has been used to prevent TGFβ-induced cell proliferation and extracellular matrix production. Decorin is therefore useful for reducing or preventing pathologies caused by TGFβ-regulated activity, such as cancer, glomerulonephritis and pathologies characterized by excess matrix. In cancer, for example, decorin can be used to destroy TGFβ-1's growth stimulating activity on the cancer cell. Decorin is also useful for reducing or inhibiting wound contraction, which involves proteins of the extracellular matrix.

Methods for expressing and purifying human recombinant decorin are known in the art, for example, as described in WO 90/00194. However, given the hydrophobic nature of decorin from the LRRS, more convenient and reproducible methods for purifying this proteoglycan from host cell contaminants have remained elusive.

After expressing human recombinant decorin, such as from decorin-expressing Chinese hamster ovary (CHO) cells, the proteoglycan can be substantially purified from the cell culture medium by the purification procedures of this invention. By using a combination of steps, and certain reagents, in particular a 2.4 to 3 molar GuHCl solution to elute decorin from a hydrophobic interactive column, the process of this invention provides a more convenient and reproducible process for purifying human recombinant decorin. To date, it provides the purest human recombinant decorin product known.

The present invention also provides a novel process for detecting the presence of guanidinium ions in a solution suspected of containing guanidinium ions, such as in protein-containing solutions where GuHCl has been used to purify the protein, as with the above purification scheme of decorin.

Guanidine is a buffer salt that is used in the purification of recombinant protein from the cellular milieu in the culture media. Residual guanidinium ions are presumed to be associated with the purified protein as a counter ion. Procedures have been designed to replace this counter ion with other ions, however, accurate determination of residual guanidinium ions in the low parts per million range is not available by current procedures, such as spectrophotometry. Residual guanidinium ion is considered to be a generally undesirable component in products designed for medicinal administration.

The invention provides an ion chromatographic method which uses a conductivity detector to detect and quantify guanidinium ions present in a solution. The method is highly sensitive, reproducible, and fast. The high sensitivity to guanidinium ions, in the parts per million range, is remarkable in the presence of an overwhelming concentration of sodium. The process of this invention also has the advantage of requiring only minimal sample volumes and can be accomplished with very little sample preparation.

SUMMARY OF THE INVENTION

The present invention is directed to a process for the production of substantially pure human recombinant decorin. The decorin purification process involves, first, contacting a decorin-containing cell culture medium with a first strong-anionic exchange resin, by loading the decorin-containing medium onto the resin in a solution having a salt concentration from about 0.1 to about 0.4 molar, washing the resin with a buffer solution having an eluting salt concentration from about 0.3 to about 0.4 molar and eluting the bound human recombinant decorin with a buffer solution having an eluting salt concentration from about 0.9 to about 1.2 molar. This is followed by contacting the resultant decorin-containing eluant fractions with a hydrophobic interactive chromatography (HIC) resin by loading the decorin-containing fractions onto the HIC resin in a solution containing about 1 to about 2 molar guanidine hydrochloride (GuHCl), washing the HIC resin with a buffer solution containing about 1 to about 2 molar GuHCl, and eluting the bound human recombinant decorin from the HIC column with a buffer solution containing about 2.4 to about 3 molar GuHCl. Lastly, the process involves diluting the decorin-containing eluant fractions from the HIC resin to a GuHCl concentration of less than about 0.3 molar, loading the diluted solution onto a second strong-anionic exchange resin, washing the second ion-exchange resin with a buffer solution having an eluting salt concentration from about 0.3 to about 0.4 molar, and eluting the bound human recombinant decorin with a buffer solution having an eluting salt concentration from about 0.9 to about 1.2 molar to obtain substantially purified human recombinant decorin.

The invention also provides a process for detecting the presence of guanidinium ions in a sample solution. The detection process involves contacting a sample solution suspected of containing guanidinium ions with a cation exchange resin and eluting the guanidinium ions present in the sample solution with an aqueous buffer solution having a pH of about 1.5 to about 2. This is followed by contacting the eluant with a cation suppressor column and simultaneously flowing a suppressor regenerate solution in the opposite direction on the opposite side of the permeable membrane of the column, and finally, detecting the presence of guanidinium ions in the eluant from the ion exchange column which was contacted with the suppressor column by use of a conductivity detector.

BRIEF DESCRIPTION OF THE DRAWINGS

FIG. 1 shows the nucleic acid and amino acid sequence of human recombinant decorin produced using decorin-expressing Chinese hamster ovary (CHO) cells.

DETAILED DESCRIPTION OF THE INVENTION

Figure 2:
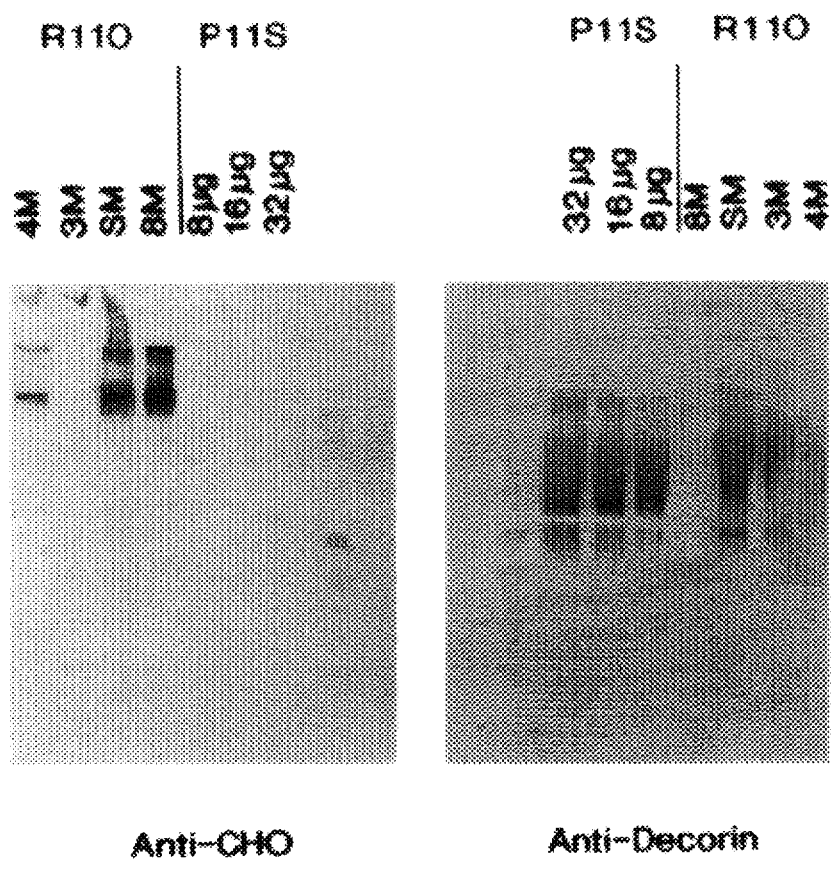
FIG. 2 shows a pair of Western blots comparing the elution of (1) decorin and (2) CHO protein from an octyl-Sepharose column using 3M and 4M GuHCl solution.

Decorin, also known as PG-II or PG-40, is a small proteoglycan produced by fibroblasts. Its core protein has a molecular weight of about 40,000 daltons. The core has been sequenced (Krusius and Ruoslahti, Proc. Natl. Acad. Sci. USA, 83:7683 (1986); which is incorporated herein by reference) and it is known to carry a single glycosaminoglycan chain of the chondroitin sulfate/dermatan sulfate type (E. Ruoslahti, Ann. Rev. Cell Biol., 4:229-255 (1988), which is incorporated herein by reference). Most of the core protein of decorin is characterized by the presence of a leucine-rich repeat (LRR) of about 24 amino acids.

As used herein, the term "human recombinant decorin" is used in its broadest sense to include the structure of native human decorin, as well as modified native human decorin, provided that the modified human decorin is a functional equivalent of native human decorin and further provided that the modified human decorin retains sufficient structural similarity to native human decorin so as be purified by the process of this invention. Functional equivalents of native human decorin include, for example, a decorin polypeptide that is structurally different from native decorin but retains the functional activity that is similar to the functional activity characteristic of native human decorin. An active fragment of native human decorin is an example of a functional equivalent of decorin. A functional equivalent of decorin also can be a decorin polypeptide that is modified, for example, by the addition of one or more side chains such as a lipid or a carbohydrate chain or by chemical modification such as phosphorylation of a side chain, provided that the modification does not interfere substantially with the function of decorin.

Specific examples of functional equivalents embraced by the term "human recombinant decorin," include those recombinant decorin products which retain all or part of the amino-terminal signal sequence and/or which have minor truncations at the carboxy terminus. For example, decorin produced using decorin-expressing CHO cells can retain a partial N-terminal signal sequence, glycine$^{-13}$ to glutamic acid$^{-1}$ (numbering from Krusius and Ruoslahti, supra) and can lack the C-terminal amino acid residue, lysine (Krusius and Ruoslahti, supra; See also FIG. 1).

As used herein, the term "substantially pure human recombinant decorin" refers to the approximate level of purity obtained by the experimental procedure described in Example I, which is at least about 95% pure and more preferably about 99% pure from other protein contaminants and contaminating nucleic acid. Purity can be measured by any known method in the art, such as by gel imaging or using a densitometer.

Methods for preparing human recombinant decorin are known in the art. For example, Ruoslahti and Yamaguchi disclose, in WO 90/00194, a method for transfecting CHO cells with human decorin cDNA (Krusius and Ruoslahti, supra). Alternatively, large scale productions of decorin can be produced by the methods of Example I.

After expressing human recombinant decorin, the proteoglycan can be substantially purified from a cell culture medium, such as a CHO medium, by the purification procedures of this invention. The process in a general sense involves the combination of three separate stages characterized by contacting decorin-containing cell culture medium with (1) a first strong anionic exchange resin; then with (2) a hydrophobic interactive chromatographic resin; and finally with (3) a second strong anionic exchange resin.

First Strong Anionic Exchange Resin:

A decorin-containing cell culture medium is initially contacted with a first strong-anionic exchange resin, by (1) loading the decorin-containing medium onto the resin in a solution having a salt concentration from about 0.1 to about 0.4 molar, (2) washing the resin with a buffer solution having a eluting salt concentration from about 0.3 to about 0.4 molar, and (3) eluting the bound human recombinant decorin with a buffer solution having a eluting salt concentration from about 0.9 to about 1.2 molar.

As used herein the term "salt" means any chemical compound formed by replacing all or part of the hydrogen ions of an acid with one or more cations of a base and which is preferably a monovalent salt, such as sodium chloride (NaCl), sodium acetate or potassium chloride (KCl). An "eluting salt," in addition to being a salt as defined above, is also capable of eluting either contaminants or decorin bound to a resin. For example, the wash with a buffer solution having a salt concentration from about 0.3 to about 0.4 molar is an "eluting salt" concentration which elutes contaminants. The elution with a buffer solution having a concentration of about 0.9 to about 1.2 molar is an "eluting salt" which elutes bound decorin. Generally the salts are contained in buffer solutions. As used herein the term "buffer solution" means a solution containing a mixture of a weak acid and its conjugate weak base that is capable of resisting substantial changes in pH upon the addition of small amounts of acidic or basic substances. Buffering agents, include for example, $Na_3PO_4$, $K_3PO_4$, NaAc, and Tris.

As used herein, the phrase "strong-anionic exchange resin" is an ion exchange resin having functional groups with a positive charge which are completely ionized over a wide pH range, such as quaternary amino groups. Examples of strong anionic exchange resins include, but are not limited to, Q-Sepharose (Pharmacia, Piscataway, N.J.), Poros Q Strong Anion (Perceptive Biosystems, Cambridge, Mass.), Toyopearl Super Q-650M (Tosohaas, Mongomery, Pa.), and Macroprep Q (BioRad, Hercules, Calif.). The preferred first strong-anionic exchange resin is Q-Sepharose.

Before applying the human recombinant decorin containing cell culture medium to the first resin, protease inhibitors which are specific for host cell proteases to be inhibited may be added to the decorin-containing cell culture medium. Protease inhibitors for CHO, as well as other host cells, are benzamidine, tetrasodium ethylenediamino tetracetic acid ($Na_4EDTA$), phenylmethylsulfonyl fluoride (PMSF) and aprotinin (a trypsin inhibitor). Where the host cells are CHO, the protease inhibitors are preferably benzamidine and $Na_4EDTA$, and usually in concentrations of about 1 millimolar benzamidine and 5 millimolar $Na_4EDTA$.

To fragment any DNA remaining in the decorin-containing eluant fractions from this initial ion-exchange purification, the fractions may be is treated with a DNAase, or 0.1 molar hydrochloric acid at low temperature 0°–4° C. or any other reagent which is capable of fragmenting DNA.

Hydrophobic Interactive Chromatographic (HIC) Resin:

The second stage of the decorin purification process involves contacting the resultant decorin-containing eluant fractions obtained by the procedures above with a hydrophobic interactive chromatography (HIC) resin, by (1) loading the decorin-containing fractions onto the HIC resin in a solution containing about 1 to about 2 molar GuHCl, (2) washing the HIC resin with a buffer solution of about 1 to about 2 molar GuHCl and which GuHCl concentration is higher than the GuHCl concentration used in the previous loading step, and (3) eluting the bound human recombinant decorin from the HIC column with a buffer solution of about 2.4 to about 3 molar GuHCl.

The HIC resin used in the invention is preferably of medium to strong hydrophobicity, which means the hydrophobic ligand of the resin has a straight or branched carbon chain length of four carbons or greater. Examples of HIC resins of medium to strong hydrophobicity, include but are not limited to, octyl-Sepharose (Pharmacia, Piscataway, N.J.). The preferred HIC resin is octyl-Sepharose. Future resins with ligands having similar hydrophobicity and chain length to the octyl ligand will be especially useful.

As described above, the term "buffer solution" means a solution containing a mixture of a weak acid and its conjugate weak base that is capable of resisting substantial changes in pH upon the addition of small amounts of acidic or basic substances. Buffering agents, include for example, $Na_3PO_4$, $K_3PO_4$, NaAc, and Tris. Generally, the pH of the buffer solution should be between pH 6 and pH 7.

To attract negatively charged contaminating nucleic acids and to dissociate decorin from residual histone DNA complex, before loading the GuHCl-containing solution onto the HIC resin, a polyamine such as spermine may be added to the solution. Alternatively, or in addition thereto, polyamine may be added to the 1 to 2 molar GuHCl buffer solution used to wash the column while decorin is bound.

Second Strong Anionic Exchange Resin:

The third stage of the purification involves contacting the decorin containing solution with yet another strong-anionic exchange resin in order to exchange guanidinium ions with other cations. This stage involves, (1) diluting the decorin-containing eluant fractions from the HIC resin to obtain a GuHCl concentration of less than about 0.3 molar and loading the diluted solution onto a second strong-anionic exchange resin, (2) washing the resin with a buffer solution having an eluting salt concentration from about 0.3 to about 0.4 molar and (3) eluting the bound human recombinant decorin with a buffer solution having an eluting salt concentration from about 0.9 to about 1.2 molar to obtain substantially purified human recombinant decorin. After this last step, the purified human recombinant decorin may be optionally diafiltered or concentrated by ultrafiltration. Ultrafiltration may be by stirred cell or tangential flow with either spiral bound or flat plate membrane.

As described above the term "salt" means any chemical compound formed by replacing all or part of the hydrogen ions of an acid with one or more cations of a base and which is preferably a monovalent salt, such as sodium chloride (NaCl), sodium acetate or potassium chloride (KCl). Also, as described above, "eluting salt," in addition to being a salt as defined above, is also capable of eluting either contaminants or decorin bound to a resin. For example, the wash with a buffer solution having a salt concentration from about 0.3 to about 0.4 molar is an "eluting salt" concentration which elutes contaminants. The elution with a buffer solution having a concentration of about 0.9 to about 1.2 molar is an "eluting salt" which elutes bound decorin. Generally the salts are contained in buffer solutions. As used herein, and as indicated above, the term "buffer solution" means a solution containing a mixture of a weak acid and its conjugate weak base that is capable of resisting substantial changes in pH upon the addition of small amounts of acidic or basic substances. Some buffering agents are $Na_3PO_4$, $K_3PO_4$, NaAc, TriS.

Also as described above the phrase "strong-anionic exchange resin" is an ion exchange resin having functional groups with a positive charge which are completely ionized over a wide pH range, such as quaternary amino groups. Examples of strong anionic exchange resins include, but are not limited to, Q-Sepharose (Pharmacia, Piscataway, N.J.), Poros Q Strong Anion (Perceptive Biosystems, Cambridge, Mass.), Toyopearl Super Q-650M (Tosohaas, Mongomery, Pa.), and Macroprep Q (BioRad, Hercules, Calif.). The preferred second-anionic exchange resin is Q-Sepharose. The first and the second strong-anionic resins may be the same or different.

In the above three general steps the fractions eluted containing decorin can be detected with U.V. spectrophotometry. For example, the U.V. detector can be set at 280 and optionally at 260 nm, as set forth in the ensuing Examples.

Furthermore, the conditions for using the resins described above (such as temperature, flow rates, column loading, buffer pH, and the like) follow the manufacturer's directions unless otherwise noted herein.

In a preferred embodiment, the process for the production of substantially pure human recombinant decorin from a decorin-containing medium comprises, first, adding protease inhibitors specific for the host cell proteases to be inhibited to the decorin-containing medium, followed by adding salt to the medium resulting from the first step to bring the concentration of such salt-containing solution to about 0.1 to about 0.4, molar applying the salt solution to a first strong-anionic exchange resin, washing the resin with a buffer solution having an eluting salt concentration from about 0.3 to about 0.4 molar, and eluting the bound human recombinant decorin from the resin with a buffer solution having an eluting salt concentration from about 0.9 to about 1.2 molar. The preferred process further comprises, adding to the decorin-containing eluant fractions from the first resin, sufficient amounts of GuHCl to bring the concentration of the resultant solution to about 1 molar to about 2 molar, applying the fractions to a HIC resin of medium to strong hydrophobicity, washing the HIC resin with a buffer solution of about 1 to about 2 molar GuHCl and which GuHCl concentration is higher than the GuHCl concentration used in the previous loading step, and eluting the bound human recombinant decorin from the HIC resin with a buffer solution of about 2.4 to about 3 molar GuHCl. Lastly, the preferred process comprises diluting the decorin-containing eluant fractions from the HIC resin to obtain a GuHCl concentration of less than about 0.3 molar, applying the diluted decorin-containing fractions to a second strong-anionic exchange resin, washing the resin with a buffer solution having an eluting salt concentration from about 0.3 to about 0.4 molar and eluting the bound human recombinant decorin-containing fractions from the resin with a buffer solution having an eluting salt concentration from about 0.9 to about 1.2 molar to recover substantially purified decorin which is optionally diafiltered or concentrated by ultrafiltration.

In a more preferred embodiment, the process for the production of substantially pure human recombinant decorin from a decorin-containing medium comprises, first, adding benzamidine and $Na_4EDTA$ to bring the decorin-containing medium to a concentration of about 1 millimolar and about 5 millimolar, respectively, followed by adding NaCl to the medium resulting from the first step to bring the concentration of such NaCl-containing solution to about 0.4 molar, applying the NaCl-containing solution to a Q-Sepharose resin, washing the Q-Sepharose resin with a NaCl buffer solution having a concentration of about 0.4 molar, and eluting the bound human recombinant decorin from the Q-Sepharose resin with a buffer solution having a NaCl concentration of about 1.0 molar. The more preferred process further comprises, adding to the decorin-containing eluant fractions from the Q-Sepharose resin, sufficient amounts of GuHCl to bring the concentration of the resultant fraction to about 1 molar, applying the decorin-containing fractions to an octyl-Sepharose resin, washing the octyl-Sepharose resin with a buffer solution of about 2 molar GuHCl, and eluting the bound human recombinant decorin from the octyl-Sepharose resin with a buffer solution of about 3 molar GuHCl. Lastly, the more preferred process comprises diluting the decorin-containing eluant fractions from the octyl-Sepharose column to obtain a GuHCl concentration of less than about 0.3 molar, applying the diluted decorin-containing fractions to a second Q-Sepharose resin, washing the Q-Sepharose resin with a buffer solution having a NaCl concentration of about 0.4 molar, and eluting the bound human recombinant decorin-containing fractions from the resin with a buffer solution having a NaCl concentration of about 1.0 molar to recover substantially purified decorin which is further concentrated by ultrafiltration.

Proteins carrying 0-linked oligosaccharides are fairly common in biological systems, and comprise a subset of contaminating proteins in cultures of cells expressing recombinant proteins. Because decorin does not carry 0-linked oligosaccharide chains, an optional step in the purification process is contacting the decorin-containing medium with a lectin column that preferentially binds 0-linked sugars. A preferred lectin for this purpose is JACALIN, which can be obtained from Vector Laboratories Inc., Burlingame, Calif. 94010.

Choi et al., *J. Biol. Chem.*, 264(5): 2876–2884 (1989), discloses isolating decorin and another proteoglycan, biglycan, from bovine and calf tissue extracts using hydrophobic interactive chromatography by eluting with 4 molar GuHCl. While Choi et al. shows separation of decorin from biglycan using these procedures, the use of 4 molar GuHCl on a HIC column is not applicable to purifying human recombinant decorin. Surprisingly and unexpectedly, lower concentrations, such as 2.4 to 3 molar, GuHCl is required. As shown in the comparative data in Example I, anti-decorin antibody detects decorin in a 3 molar eluant but not in a 4 molar eluant. Further, anti-CHO antibody detects contaminating host cell proteins in the 4 molar eluant but not the 3 molar eluant.

The present invention also provides a novel process for detecting the presence of guanidinium or guanidine ions in a solution suspected of containing such ions, such as in protein-containing solutions where GuHCl has been used to purify the protein, as with the above purification scheme of decorin.

The invention provides a process for detecting the presence of guanidinium ions in a sample solution by contacting a sample solution suspected of containing guanidinium ions with a cation exchange resin and eluting the guanidinium ions present in the sample solution with an aqueous buffer solution having a pH of about 1.5 to about 2. This is followed by contacting the eluant with a cation suppressor column and simultaneously flowing a suppressor regenerate solution in the opposite direction on the opposite side of the permeable membrane of the column, and finally, detecting the presence of guanidinium ions in the eluant from the ion exchange resin which was contacted with the suppressor column by use of a conductivity detector.

As used herein, the term "detecting" means both quantitatively and qualitatively determining the presence of guanidinium ions (Gu+) in a solution suspected of containing guanidinium ions. When the amount of Gu+ is less than the minimal level of detection, generally 3 parts per million (ppm), detection is qualitative. Above 3 parts per million, the detection is generally quantitative.

As used herein the phrase "a sample solution suspected of containing guanidinium ions" means any type of solution which may contain guanidinium ions or guinidine ions (Gu+), protein-containing, or otherwise. While the Gu+ is preferably detected in protein-containing solutions, such as a solution comprising human recombinant decorin, there is nothing in the process of this invention which limits its applicability to solutions containing proteins.

As used herein the term "cation exchange resin" is any ion exchange resin with a fixed negative charge, such as resins with carboxyl or sulfonate groups. Although the preferred resins are Dionex Ionpac resins (Dionex, Sunnyvale, Calif.), such as CS12 (carboxyl) or CS10 (sulfonate), other cation ion exchangers may be used, including, but are not limited to, Poros CM (carboxymethyl) (University Park at MIT Cambridge, Mass.).

Guanidinium ions are eluted from the cation exchange resin with an aqueous solution having a pH of about 1.5 to about 2.0. Preferably, the aqueous solution is an aqueous buffer containing about 10 millimolar concentration of hydrochloric acid, about 2 millimolar concentration of diamniopropoinic acid (DAP), and has a final pH of about 1.5.

The eluant from the cation exchange column is contacted with a cation suppressor column which is simultaneously flowing a suppressor regenerate solution in the opposite direction on the opposite side of the permeable membrane of the column. Any cation suppressor column known in the art may be used, which generally contains a suppressor bed system with a permeable membrane having 500 times the ion strength to absorb $H^+$ ions and allow $Gu^+$ detection. The preferred column is a Dionex Cation MicroMembrane Suppressor (Dionex, Sunnyvale, Calif.). The suppressor regenerate solution is preferably an aqueous solution of about 100 millimolar tetrabutylammonium hydroxide. The presence of guanidinium ions in the eluant from the cation exchanger that was contacted with the suppressor column is detected using a conductivity detector.

With a conductivity detector, a solution flows between the anode and cathode. The amount of charge present determines the conductivity, which is proportional to the concentration of an ion. Conductivity is increased with increasing ion concentration. Conductivity detectors include, for example, those manufactured by Dionex (Sunnyvale, Calif.), such as the Dionex Bio/LC ion chromatography detector, and the Alltech Model 320 conductivity detector (Alltech, San Jose, Calif. or Deerfield, Ill.). Generally the conditions should be such that background ion strength is low enough so that background noise does not interfere with reading the amount of ion present.

Decorin has been used to prevent TGFβ-induced cell proliferation and extracellular matrix production (see, for example, Yamaguchi and Ruoslahti, *Nature* 336:224(1988); Border et al., *Nature* 360:361 (1992), both of which are incorporated herein by reference). Decorin can bind TGFβ and is therefore useful for purifying TGFβ. In addition to binding TGFβ, decorin can inhibit TGFβ activities. Thus, decorin is useful for reducing or preventing pathologies caused by TGFβ-regulated activity. Specific examples of pathologies which can be treated include cancer, fibrotic diseases, including dermal and internal scarring, and glomerulonephritis. In cancer, for example, decorin can be used to destroy TGFβ-1's growth stimulating activity on the cancer cell. Decorin also can bind collagen and affect collagen fibril formation, and it is also useful for reducing or inhibiting wound contraction (see, for example, John Harper, *Wounds*, 6(2):70 (1994) which is incorporated herein by reference).

Pharmaceutical compositions comprising decorin purified by this invention can be useful for the above-mentioned purposes. Pharmaceutically acceptable carriers are well known in the art and include aqueous solutions such as physiologically buffered saline or other solvents or vehicles such as glycols, glycerol, vegetable oils (eg., olive oil) or injectable organic esters. A pharmaceutically acceptable carrier can be used to administer the decorin polypeptide to a cell in vitro or to a subject in vivo.

A pharmaceutically acceptable carrier can contain a physiologically acceptable compound that acts, for example, to stabilize the polypeptide or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide and on the particular physiochemical characteristics of the specific polypeptide. For example, a physiologically acceptable compound such as aluminum monosterate or gelatin is particularly useful as a delaying agent, which prolongs the rate of absorption of a pharmaceutical composition administered to a subject.

A pharmaceutical composition comprising an effective amount of decorin can be administered to a subject by various routes including, for example, topically, orally or parenterally, such as intravenously, intramuscularly, subcutaneously, intraperitoneally or by passive or facilitated absorption through the skin using, for example, a skin patch or transdermal iontophoresis, respectively. Topical administration can be passive, for example, by direct application of an ointment or powder, or active, for example, using a nasal spray or inhalant. Where the composition is administered as a topical spray, one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

An effective amount of the pharmaceutical composition comprising decorin is generally in the range of about 0.01 to 100 mg/kg body weight. An effective amount can be determined using methods known to those in the art. The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the amount of decorin required to obtain an effective dose in a subject depends on many factors including the age and general health of the subject as well as the route of administration and the number of treatments to be administered.

The following examples are intended to illustrate but not limit the present invention.

EXAMPLE I

PREPARATION OF SUBSTANTIALLY PURE DECORIN

This example demonstrates production of substantially pure human recombinant decorin.

EXPRESSION SYSTEM

Decorin was produced using decorin-expressing CHO cells as follows. The 1.8 kb full-length decorin cDNA described in Krusius and Ruoslahti, Proc. Natl. Acad. Sci. USA 83:7683 (1986), which is incorporated herein by reference, was used for the construction of decorin expression vectors. For the expression of decorin core protein, cDNA was mutagenized so the fourth codon, TCT, coding for serine, was changed to ACT coding for threonine, or GCT coding for alanine. This was engineered by site-directed mutagenesis according to the method of Kunkel, Proc. Natl. Acad. Sci USA 82:488 (1985), which is incorporated herein by reference. The presence of the appropriate mutation was verified by DNA sequencing.

The mammalian expression vectors pSV2-decorin and pSV2-decorin/CP-thr4 core protein were constructed by ligating the decorin cDNA or the mutagenized decorin cDNA into 3.4 kb HindIII-Bam HI fragment of pSV2 (Mulligan and Berg, Science 209:1423 (1980), which is incorporated herein by reference).

Dihydrofolate reductase (dhfr)-negative CHO cells (CHO-DG44) were cotransfected with pSV2-decorin or pSV2-decorin/CP and pSV2dhfr by the calcium phosphate coprecipitation method. The CHO-DG44 cells transfected with pSV2-decorin are deposited with the American Type Culture Collection under Accession Number ATCC No. CRL 10332. The transfected cells were cultured in nucleoside-minus alpha-modified minimal essential medium (α-MEM), (GIBCO, Long Island) supplemented with 9% dialyzed fetal calf serum, 2 mM glutamine, 100 units/ml penicillin and 100 μg/ml streptomycin. Colonies arising from transfected cells were picked using cloning cylinders, expanded and checked for the expression of decorin by immunoprecipitation from $^{35}SO_4$-labeled culture supernatants. Clones expressing a substantial amount of decorin were then subjected to gene amplification by stepwise increasing concentration of methotrexate (MTX) up to 0.64 μM (Kaufman and Sharp, J. Mol. Biol. 159:601 (1982), which is incorporated herein by reference). All the amplified cell lines were cloned either by limiting dilution or by picking single MTX resistant colonies. Stock cultures of these established cell lines were kept in MTX-containing medium. Before use in protein production, cells were subcultured in MTX-minus medium from stock cultures and passed at least once in this medium to eliminate the possible MTX effects.

Alternatively, larger scale productions of decorin were performed using CHO cells attached to microcarrier beads. Decorin-expressing CHO cells as described above were allowed to adhere to microcarrier beads, then were cultured in suspension. Once a seed culture of decorin-expressing cells was established, the fermentation reaction vessel was seeded and the growth phase of fermentation continued until the desired cell density was achieved. At that time, fresh medium was slowly perfused into the reactor vessel and conditioned medium was collected at a rate of about 80–85% of the reactor volume per day. Care was taken to separate cell-containing microcarriers from the perfusate so as not to lose decorin-producing cells. The harvest medium was incubated at 4° C. for 24 hours prior to filtration to allow cell debris to settle out.

PURIFICATION OF DECORIN

Decorin was purified from 40 liters of CHO cell culture medium as described above. A solution of benzamidine and Na$_4$EDTA was added to a final concentration of 1× in the medium (100× solution is 100 mM benzamidine and 500 mM Na$_4$EDTA). The medium was filtered with Whatman #1 filter paper and the NaCl concentration was adjusted to 0.4 NaCl.

A Q-Sepharose column was prepared by washing 300 ml resin (Q-Sepharose fast flow gel; Pharmacia, Piscataway N.J.) in a fritted disc glass funnel with 10 column volume deionized water to remove ethanol. The Q-Sepharose was degassed and placed into a 10 cm×30 cm column with a flow adapter (Watson/Marlow Peristaltic Pump with 9.6 mm ID tubing). The bubble trap and pump were connected to the column, which then was equilibrated at a flow rate of 200 ml/min with 10 column volume buffer A (25 mM Tris, pH 7.8, 0.4M NaCl). UV absorbance at 280 nm, 1.0 AUFS (Absorbance units, full scale) was determined; the detector was set to zero using buffer A.

Cell culture medium was loaded onto the column at flow rate of 200 ml/min and the flow through was collected. The column was washed with buffer A ((1 liter). The column was eluted with buffer B ((1.5 liter) 25 mM Tris, pH 7.8, 1M NaCl) and one minute fractions were collected. The eluted peak was pooled, the volume was recorded (usually 1–1.5 liters) and absorbance at 280 nm and at 260 nm was determined. The latter reading was used to detect nucleic acid co-eluted with decorin on the Q-Sepharose column. One volume (equal to the pooled volume) 2M guanidine-HCl (GuHCl) was added and the sample was loaded onto an Octyl-Sepharose column.

The Octyl-Sepharose column was prepared by washing 60 ml Octyl-Sepharose gel (Pharmacia) with 10 column volume deionized water in a sintered glass funnel to remove EtOH. The gel was degassed and placed in a 2.6 cm×30 cm water jacketed column with two flow adapters (Pharmacia), which compacted and retained the gel in position. The column was maintained at 25° C. with a refrigerated circulator. The UV monitor (280 nm) was connected and was set to zero with buffer C ((10 column volume or 600 ml) 0.1 NaOAc, pH 6.3, 1M GuHCl; filtered with 0.2 μM acetate filter and degassed).

The fraction collected from the Q-Sepharose column was loaded onto the Octyl-Sepharose column at a flow rate of 3 ml/min and samples were collected at 2 min/fraction (6 ml/tube). The column was washed with buffer C, until the baseline was established, then with buffer D (0.1M NaOAc, pH 6.3, 2M GuHCl; filtered with 0.2 μM acetate filter, then degassed) until the same baseline was established.

Decorin was eluted using buffer E ((200 ml) 0.1M NaOAc, pH 6.3, 3M GuHCl) at a flow rate of 3 ml/min. A small amount of protein contaminant eluted with the decorin. An elution profile was performed on the fractions by determining the absorbance at 280 nm and 260 nm to show that most of O.D. 280 absorbance was due to decorin and not to nucleic acid. The column then was eluted using buffer F ((150 ml) 0.1M NaOAc, pH 6.3, 4M GuHCl; filtered with 0.2 μM acetate filter, then degassed), to remove an unidentified 200 kDa protein and some histone proteins. The column was stripped with of buffer G ((150 ml) 0.1M NaOAc, pH 6.3, 8M GuHCl; filtered with 0.2 μM acetate filter, then degassed) to remove more host cells contaminating proteins.

The 3M GuHCl fraction containing decorin was diluted 1:10 with a solution containing 50 mM NaPO$_4$ at pH 7.4. A Q-Sepharose column (Pharmacia) was equilibrated with a buffer, 50 mM NaPO$_4$ (pH 7.4), 0.4M NaCl, and the diluted decorin solution was pumped (Minipuls 2 peristaltic pump with 1.52 ID PVC manifold tubing; Gilson; Middleton Wis.) onto the column at a rate of 3 ml/min. The column was washed with five column volumes of the same buffer, then decorin was eluted with additional buffer, 50 mM NaPO$_4$ (pH 7.4)/1.0M NaCl. The eluant was concentrated/diafiltered by ultrafiltration (Amicon Inc., Beverly, Mass.)

Levels of residual nucleic acid and GuHCl in the final preparation were evaluated by a DNA assay and a GuHCl assay, respectively, as described below. Decorin was quantitated by amino acid analysis and a direct ELISA, as described below.

FIG. 2 provides comparative data which exemplifies that human recombinant decorin can be purified on a HIC resin in 3 molar GuHCl but not 4 molar GuHCl. FIG. 2 shows a pair of Western blots comparing the elution of (1) decorin and (2) Chinese hamster ovary (CHO) protein from an octyl-Sepharose column using 3M and 4M GuHCl.

The first Western anti-CHO blot shows from left to right the 4M eluate having some CHO host cell protein (HCP) contaminant, the 3M eluate having little or no CHO HCP contaminant, the highly contaminated starting material (SM) and the 8M strip (the last step) bringing off the majority of the CHO HCP.

The second Western anti-decorin blot shows, from left to right, the 8M strip having very little decorin, the starting material (SM), the 3M eluate containing the majority of the decorin eluted, and finally a trace of decorin eluted with 4M GuHCl.

DNA ASSAY PROTOCOL

Decorin samples produced by the above recombinant and purification procedures are tested for DNA content as follows. The decorin samples were first prepared for the DNA assay protocol, followed by denaturation, blotting, hybridization, and detection of DNA.

Sample Preparation: Samples were prepared for the assay by digesting of proteins with a protease, precipitating digested peptides with Ethachinmate, and diluting the samples. Samples of CHO genomic DNA for a standard curve were also prepared as described below.

Due to dilution of the samples prior to blotting, the DNA assay protocol used was based upon small sample volumes. The volume of decorin samples can be increased (to 1.0 ml, if required) once the DNA concentration is significantly lower. All other reagent volumes need to be changed accordingly, including the concentrations and volumes of the DNA spiked samples (described below).

Decorin samples (non-spiked) were prepared as follows: 50 μl of decorin sample; 34 μl of sterile water; 10 μl of 100 mM Tris-Cl, 100 mM EDTA (pH 7.5); 5 μl of 10% SDS; and 1 μl of 20 mg/ml Proteinase K (Boehringer Mannheim, Chicago, Ill. Cat. #161519, or equivalent) were combined for a final volume of 100 μl.

To confirm good recovery of DNA in the samples after proteinase K and ethachinmate treatment, DNA is spiked into some samples prior to treatment. For example, samples to later be diluted to 1:100 and 1:400 were spiked to 6.4 ng DNA so that after dilution the spikes were 64 pg and 16 pg, respectively. Concentrations used for the spiked samples, which are later diluted to 1:100 and 1:400, were as follows: 50 μl of decorin sample; 10 μl of DNA spike (640 ng/ml); 24 μl of sterile water; 10 μl of 100 mM Tris-Cl, 100 mM EDTA (pH 7.5); 5 μl 10% SDS; and 1 μl of 20 mg/ml Proteinase K were combined for a final volume of 100 μl. A 50 μl spike control of the 64 pg/ml (50 μl of the 128 pg/ml can be used), not containing any decorin, was also prepared.

The decorin samples (+/– spike) treated with proteinase K (described above) were incubated at 37° C. for 2 hours for protein removal. After deproteination, ethachinmate was used to precipitate the digested proteins as follows. Samples were prepared from 100 µl of deproteinated sample (+/– spike); 300 µl (3 volumes) of 6M NaCl; 1 µl (vortexed thoroughly) of Ethachinmate (Nippon Gene, Cat. #9301F) to which 400 µl (equal volume) of 100% of ethanol was added. The samples were vortexed and spun at 15,000 rpm (microfuge) for 15 minutes. The pellets were dried in vacuo and then redissolved in 50 µl (equal to starting volume) TE buffer (10 mM Tris-Cl, 1 mM EDTA, pH 7.5).

Following Ethachinmate precipitation, the samples were diluted in TE buffer. The dilutions depended on the estimated DNA contamination level. At least two dilutions per sample were tested.

Samples for a standard curve (hereinafter "standards") were also made. The standard curve started at 256 pg and was diluted 2-fold to 4 pg. There were two standard curves per blot in case of any problems with individual spots on the film. Therefore, to have sufficient volumes for two sets, the following dilution method was used: a standard solution containing 256 pg DNA consisted of 200 µl 10 ng/ml genomic DNA+580 µl TE buffer for a concentration of 2560 pg/ml; standard 128 pg consisted of 250 µl 256 standard+ 250 µl TE buffer for a concentration of 1280 pg/ml; standard 64 pg consisted of 250 µl 128 pg standard+250 µl TE buffer for a concentration of 640 pg/ml; standard 32 pg consisted of 250 µl 64 pg standard+250 µl TE buffer for a concentration of 320 pg/ml; standard 16 pg consisted of 250 µl 32 pg standard+250 µl TE buffer for a concentration of 160 pg/ml; standard 8 pg consisted of 250 µl 16 pg standard+250 µl TE buffer for a concentration of 80 pg/ml; and standard 4 pg consisted of 250 µl 8 pg standard+250 µl TE buffer for a concentration of 40 pg/ml.

Denaturation: To denature the samples (+/– spikes) 200 µl of each sample dilution was added to 200 µl 6M KSCN solution (which had been run through a 0.22µ filter before use) and heated to 96° C. for 10 minutes. The samples were immediately put on ice, and once chilled, spun briefly (2–3 seconds) in a microfuge and then loaded onto 200 µl/slot.

To denature standards, 300 µl of each standard dilution was added to 300 µl 6M KSCN (also filtered through 0.22µ filter) and heated to 96° C. for 10 minutes. The samples were immediately put on ice, and once chilled, spun briefly (2–3 seconds) in a microfuge then loaded onto 200 µl/slot. This procedure allowed enough of each standard for 2 curves per blot.

Blotting: Following the denaturation procedure, the samples (+/– spike) and standards were transferred, as described above, to the slot blot apparatus which was fitted with a neutral nylon membrane (Biodyne A, VWR Brisbane, Calif.) pre-wetted with 1× SSC. The DNA was fixed to the membrane using the automatic setting on the UV Stratalinker 1800 (Stratagene San Diego, Calif.). After fixation, the membranes were subjected to a series of washes, 50 ml/wash: first with autoclaved water (2 times, 10 minutes each), second with 70% ethanol (2 times, 10 minutes each), and lastly with 0.25% acetic acid/0.1M triethanolamine (2 times, 10 minutes each). The membrane was either stored at 4° until further processed or immediately processed for hybridization.

Hybridization: The membrane was prehybridized with 10 ml hybridization buffer (5× SSC, 1% I-Block™ (TROPIX, Bedford, Mass. Cat. #AB100), 0.1% N-Lauroylsarcosine, 0.02% SDS, dissolved at 60° C. for 1 hour and stored at –20° C., and which was thawed, pre-heated and pre-equilibrated to 60° C. before use) in a sealed bag at 60° C. for 1 hour.

After prehybridization, the membrane was transferred to a fresh bag. 100 µl of 500 ng/ml of the DIG-labeled DNA probe (prepared using the same genomic DNA as the standard with Boehringer Mannheim random-primer DNA Labeling Kit (Cat. #1093657, Kit #1 Indianapolis, Ind.) as directed by the vendor and then diluted to 500 ng/ml with TE buffer and stored at –20° C. in 100 µl aliquots) was denatured by incubation for 10 minutes at 96° C. random-primer. After denaturation of the probe, a small volume (approximately 1 ml) of hybridization buffer (pre-equilibrated to 60° C.) was rapidly mixed with the probe and the diluted probe was quickly added to 9.0 ml of extra hybridization buffer kept at 60° C., mixed and added to the bag. The sealed bag was then incubated overnight (15–18 hours) at 60° C., with shaking.

Following hybridization, the membrane was washed first in 50 ml of 2× SSC/0.1% SDS (2 times, 10 minutes each) and, second, in 50 ml of 0.2× SSC/0.1% SDS (2 times, 10 minutes each).

Detection by Chemiluminescence: The membrane was blocked for 30 minutes in 50 ml Blocking Solution (1× PBS, 0.2% I-Block™, 0.1% Tween-20). The membrane was transferred to fresh Blocking Solution and alkaline phosphatase conjugated anti-DIG Fab fragments (Boehringer Mannheim, Indianapolis, Ind. Cat. #1093-274) were added to the solution for a final concentration of 0.15 units/ml and total volume of 50 ml. The membrane was incubated for 30 minutes with the antibody solution and then washed for 10 minutes in 50 ml of fresh Blocking Solution. A series of washes was then performed using Wash Buffer (1× PBS, 0.3% Tween-20). Each wash used 50 ml of Wash Buffer 4 times for 5 minutes each. After washing, the membrane was equilibrated in 50 ml of AMPPD Solvent (0.1M diethanolamine, 0.02% $NaN_3$, 1 mM $MgCl_2$, pH 10.0) for 5 minutes with shaking. The solvent was replaced with AMPPD Substrate Solution (0.24 mM of AMPPD™ (TROPIX, Bedford, Mass. Cat #PD250) or Lumigen PPD™ (Boehringer Mannheim, Cat #1357-328) in AMPPD Solvent) (100 µg/ml, final concentration of AMPPD) and the reaction was kept to a minimum (10–15 ml, in a smaller dish) to conserve the AMPPD substrate. The excess substrate solution was blotted from the membrane. The membrane was sealed in a plastic bag and immediately put on X-ray film. The exposure time was from 4–5 hours.

As shown in Table 1 below, three lots of decorin samples prepared by the above recombinant and purification procedures and analyzed with this DNA assay protocol contained the following amounts of DNA: Sample 1 (1:100), 800 ng/mg protein; Sample 2 (1:100), 800 ng/mg protein; and Sample 3 (1:45), 126 ng/mg protein.

PROTOCOL FOR THE DIRECT DECORIN ELISA

Human recombinant decorin produced from by the above recombinant and purification procedures was detected and quantified using a direct decorin ELISA as follows. Immulon-2 flat bottom plates were coated with dilutions of a decorin standard and unknown samples. Dilutions were made in 0.1M $HCO_3$ ((500 mls) 1.38 g $Na_2CO_3$; 3.11 g $NaHCO_3$; volume brought up with $ddH_2O$; the pH checked at 9.6; the solutions filtered, sterilized, and stored at 4° C.), pH 9.6, in borosilicate glass tubes and each set was plated immediately after dilution. Concentration of the decorin standard set started at 19 ng/ml and was serially diluted 1:1.5 down to 1.7 ng/ml. Samples of unknown decorin concentration were diluted to fall somewhere along the standard curve, usually for purified decorin the dilution range was $1\times10^5$ to $16\times10^5$ as two-fold dilutions. The volume used was 100 µl/well. Plates were incubated at 4° C. overnight and sealed.

The coating solution was flicked out and 200 μl 1× PBS+1% BSA ((100 mls) 90 ml ddH$_2$O; 10 ml 10× PBS ((1 liter) 80 g NaCl; 2 g KCl; 6.1 g Na2HPO4; 2 g KH2PO4; volume brought up with ddH2)); 1 g Bovine Serum Albumin; solution made fresh the day of the assay) was added per well and incubated at 37° C. for 0.5–1.0 hours. The wells were then washed three times with 1× PBS+0.1% Tween-20.

A 100 μl/well aliquot of rabbit anti-decorin antibody (anti-PG40 (described in WO 91/10727 obtained from La Jolla Cancer Research Foundation) at 1:1000) was added. The antibody was diluted in 1× PBS+0.1% BSA+0.1% Tween-20 ((100 mls) 90 ml ddH$_2$O; 10 ml 10× PBS; 0.1 g Bovine Serum Albumin; 0.1 ml Tween-20; solution made fresh the day of the assay) and incubated at 37° C. for 60 minutes. The wells were washed three times with 1× PBS+ 0.1% Tween-20 ((1 liter) 900 ml ddH$_2$O; 100 ml 10× PBS; 1 ml Tween-20; solution made fresh the day of the assay).

A 100 μl/well of GoatαRb-Horse Radish Peroxidase (BioRad (Richmond, Va.) or Promega Tustin, Calif.) diluted 1:3000 with 1× PBS+0.1% BSA+0.1% Tween-20 was added and incubated at 37° C. for 60 minutes. The wells were then washed five times with 1× PBS+0.1% Tween-20. Two hundred μl per well of freshly made o-phenylenediamine dihydrochloride (OPD) solution (25 mls 0.1M Citrate Phosphate Buffer ((500 mls) 5 g citric acid; 7 g Na$_2$HPO$_4$ (anhydrous); volume brought up with ddH$_2$O, pH checked at 5.0; filtered, sterilized and stored at 4° C.); 1 10 mg OPD tablet (Sigma) 6 μl 30% H$_2$O$_2$) was then added and incubated at room temperature in the dark for 15 minutes. Fifty microliters per well of 7.8 H$_2$SO$_4$ (55 mls 36M H$_2$SO$_4$; 200 mls distilled water) was added to stop the reaction. The data was read at OD 490 and analyzed using a linear fit of the data. The highest points of the curve were eliminated if the assay started to "top out."

As shown in Table 1 below, three lots of decorin samples prepared by the above recombinant and purification procedures of Example I contained 0.82 mg/ml, 1.23 mg/ml, and 1.43 mg/ml of decorin.

EXAMPLE II

GUANIDINIUM ION ASSAY

This Example illustrates detecting and quantifying the presence of residual guanidinium ions associated with proteins purified using buffers containing guanidine in a purification process.

Standard solutions, each containing just one cation, sodium (Na+), potassium (K+), and guanidinium (Gu+) were prepared and analyzed. Serial dilutions from a stock of 1 mg/ml concentration were used to establish standard curves for each ion. Data points for the standard curve were the average of three runs. In addition, a mixture of these three cations, Na+, K+, and Gu+, were run to confirm resolution between these ions. The linear range of the guanidinium standard curve was 3.9 to 125 ppm with an r value >0.999. The guanidinium ion concentration as low as 3 ppm could be detected.

The Dionex CS 12 Cation Exchange 2 millimeter bore resin (Dionex Ionpac resin; Dionex Corporation, Sunnyvale, Calif.) was used for this assay. The associated guard column CG 12 was also employed to prolong the column performance. To keep guanidine as a cation, a buffer system of 10 millimolar hydrochloric acid (HCl) in water with 2 millimolar diaminopropionic acid (DAP) at a pH of 1.5 was used. Aliquots, up to 25 μl, of solutions containing the purified decorin produced by the procedure of Example I, at a concentration of 1–4 mg/ml were directly injected into the Dionex Ionpac resin system without prior treatment. Since the column was run isocratically, at a flow rate of 0.2 ml per minute, samples could be injected sequentially without washing and equilibrating between each sample. The sodium and guanidinium cations were well resolved from each other, with guanidinium ions eluting five minutes after the sodium peak.

The eluant from the cation exchange resin was then contacted with a cation suppressor column and guanidinium ions were detected and quantified with a conductivity detector as follows. A Dionex CMMII Cation Suppressor column with 100 millimolar tetrabutylammonium hydroxide (TBAOH) as the suppressor regenerate flowing at a rate of 3–5 ml/min was used. The output sensitivity was set at 100 uS for the conductivity detector (Dionex Bio/LC ion chromatograph detector, Dionex, Sunnyvale, Calif.). The suppressor has two different liquid streams flowing in opposite directions separated by a permeable membrane. The column eluate stream flows through the suppressor and into the detector. The regenerate stream flows through the suppressor on the opposite side of the membrane and in the opposite direction. The high concentration of OH in the suppressor feed, extracts the H+ from the eluting buffer, leaving just the sodium, potassium, and guanidinium cations to be detected.

As shown in Table 1 below, three lots of decorin samples prepared by the procedures in Example I all contained less than 3 parts per million (ppm) of guanidinium ions.

TABLE 1

| Results from Gaunidinium Ion Assay, Decorin ELISA Assay, and DNA Assay | | |
|---|---|---|
| Sample No. | Guanidinium Ion Assay | Decorin ELISA Assay | DNA Assay |
| 1 | <3 PPM | 0.82 mg/ml | 800 ng/mg protein |
| 2 | <3 PPM | 1.23 mg/ml | 800 ng/mg protein |
| 3 | <3 PPM | 1.43 mg/ml | 126 ng/mg protein |

Although the invention has been described with reference to the examples provided above, it should be understood that various modifications can be made without departing from the spirit of the invention. Accordingly, the invention is limited only by the claims.

We claim:

1. A process for detecting the presence of guanidinium ions in a protein-containing sample solution suspected of containing guanidinium ions and other cations, which comprises:
   (a) contacting the protein-containing sample solution suspected of containing guanidinium ions and other cations with a cation exchange resin;
   (b) eluting the guanidinium ions present in the sample solution with an aqueous buffer solution having a pH of about 1.5 to about 2.0;
   (c) contacting the eluant from step (b) with a cation suppressor column and simultaneously flowing a suppressor regenerate solution in the opposite direction on the opposite side of the permeable membrane in the column;
   (d) detecting the presence of guanidinium ions in the eluant of step (b) that was contacted with the suppressor column of step (c) by the use of a conductivity detector.

2. A process of claim 1 wherein the protein-containing solution comprises human recombinant decorin.

3. A process of claim 1, wherein the cation exchange resin is a Dionex Ionpac resin.

4. A process of claim 1, wherein the aqueous solution of step (b) is an aqueous buffer containing about a 10 millimolar concentration of hydrochloric acid, about a 2 millimolar concentration of diaminopropionic acid, and has a final pH of about 1.5.

5. A process of claim 1, wherein the suppressor regenerate solution of step (c) is a solution aqueous containing tetrabutylammonium hydroxide in a concentration of about 100 millimolar.

6. A process of claim 1, wherein the cation suppressor column is a Dionex Cation MicroMembrane Suppressor.

* * * * *

UNITED STATES PATENT AND TRADEMARK OFFICE
CERTIFICATE OF CORRECTION

PATENT NO. : 5,763,276
DATED : June 9, 1998
INVENTOR(S) : Craig et al.

It is certified that error appears in the above-identified patent and that said Letters Patent is hereby corrected as shown below:

Title page,
Item [54], please delete "GUANDINIUM" and replace with -- GUANIDINIUM --.

Item [75], please delete William S. Craig; John R. Harper, both of San Diego; Sam D. Hernandez, Carlsbad; Paul J. Kostel, San Diego; Jonathan R. Parker, Jamul; Thomas S. Vedvick, Carlsbad, all of Calif." and replace with
-- William S. Craig, San Diego; Sam D. Hernandez; Thomas S. Vedvick, both of Carlsbad, all of Calif. --.

Column 1,
Line 3, please delete "GUANDINIUM" and replace with -- GUANIDINIUM --.

Column 15,
Line 4, please delete "ddH2));" and replace with -- ddH$_2$O); --.

Signed and Sealed this

Sixth Day of November, 2001

Attest:

NICHOLAS P. GODICI
Attesting Officer    Acting Director of the United States Patent and Trademark Office

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
  (A) LENGTH: 1026 base pairs
  (B) TYPE: nucleic acid
  (C) STRANDEDNESS: single
  (D) TOPOLOGY: linear (ix) FEATURE:
  (A) NAME/KEY: CDS
  (B) LOCATION: 1..1026

(xi) SEQUENCE DESCRIPTION: SEQ ID NO:1:

| GGA | CCG | TTT | CAA | CAG | AGA | GGC | TTA | TTT | GAC | TTT | ATG | CTA | GAA | GAT | GAG | 48 |
| Gly | Pro | Phe | Gln | Gln | Arg | Gly | Leu | Phe | Asp | Phe | Met | Leu | Glu | Asp | Glu | |
| 1 | | | | 5 | | | | | 10 | | | | | 15 | | |

| GCT | TCT | GGG | ATA | GGC | CCA | GAA | GTT | CCT | GAT | GAC | CGC | GAC | TTC | GAG | CCC | 96 |
| Ala | Ser | Gly | Ile | Gly | Pro | Glu | Val | Pro | Asp | Asp | Arg | Asp | Phe | Glu | Pro | |
| | | | 20 | | | | 25 | | | | | 30 | | | | |

| TCC | CTA | GGC | CCA | GTG | TGC | CCC | TTC | CGC | TGT | CAA | TGC | CAT | CTT | CGA | GTG | 144 |
| Ser | Leu | Gly | Pro | Val | Cys | Pro | Phe | Arg | Cys | Gln | Cys | His | Leu | Arg | Val | |
| | | 35 | | | | 40 | | | | | 45 | | | | | |

| GTC | CAG | TGT | TCT | GAT | TTG | GGT | CTG | GAC | AAA | GTG | CCA | AAG | GAT | CTT | CCC | 192 |
| Val | Gln | Cys | Ser | Asp | Leu | Gly | Leu | Asp | Lys | Val | Pro | Lys | Asp | Leu | Pro | |
| | 50 | | | | | 55 | | | | | 60 | | | | | |

| CCT | GAC | ACA | ACT | CTG | CTA | GAC | CTG | CAA | AAC | AAC | AAA | ATA | ACC | GAA | ATC | 240 |
| Pro | Asp | Thr | Thr | Leu | Leu | Asp | Leu | Gln | Asn | Asn | Lys | Ile | Thr | Glu | Ile | |
| 65 | | | | | 70 | | | | | 75 | | | | | 80 | |

| AAA | GAT | GGA | GAC | TTT | AAG | AAC | CTG | AAG | AAC | CTT | CAC | GCA | TTG | ATT | CTT | 288 |
| Lys | Asp | Gly | Asp | Phe | Lys | Asn | Leu | Lys | Asn | Leu | His | Ala | Leu | Ile | Leu | |
| | | | | 85 | | | | | 90 | | | | | 95 | | |

| GTC | AAC | AAT | AAA | ATT | AGC | AAA | GTT | AGT | CCT | GGA | GCA | TTT | ACA | CCT | TTG | 336 |
| Val | Asn | Asn | Lys | Ile | Ser | Lys | Val | Ser | Pro | Gly | Ala | Phe | Thr | Pro | Leu | |
| | | | 100 | | | | 105 | | | | | 110 | | | | |

| GTG | AAG | TTG | GAA | CGA | CTT | TAT | CTG | TCC | AAG | AAT | CAG | CTG | AAG | GAA | TTG | 384 |
| Val | Lys | Leu | Glu | Arg | Leu | Tyr | Leu | Ser | Lys | Asn | Gln | Leu | Lys | Glu | Leu | |
| | | 115 | | | | 120 | | | | | 125 | | | | | |

| CCA | GAA | AAA | ATG | CCC | AAA | ACT | CTT | CAG | GAG | CTG | CGT | GCC | CAT | GAG | AAT | 432 |
| Pro | Glu | Lys | Met | Pro | Lys | Thr | Leu | Gln | Glu | Leu | Arg | Ala | His | Glu | Asn | |
| | 130 | | | | | 135 | | | | | 140 | | | | | |

| GAG | ATC | ACC | AAA | GTG | CGA | AAA | GTT | ACT | TTC | AAT | GGA | CTG | AAC | CAG | ATG | 480 |
| Glu | Ile | Thr | Lys | Val | Arg | Lys | Val | Thr | Phe | Asn | Gly | Leu | Asn | Gln | Met | |
| 145 | | | | | 150 | | | | | 155 | | | | | 160 | |

| ATT | GTC | ATA | GAA | CTG | GGC | ACC | AAT | CCG | CTG | AAG | AGC | TCA | GGA | ATT | GAA | 528 |
| Ile | Val | Ile | Glu | Leu | Gly | Thr | Asn | Pro | Leu | Lys | Ser | Ser | Gly | Ile | Glu | |
| | | | | 165 | | | | | 170 | | | | | 175 | | |

| AAT | GGG | GCT | TTC | CAG | GGA | ATG | AAG | AAG | CTC | TCC | TAC | ATC | CGC | ATT | GCT | 576 |
| Asn | Gly | Ala | Phe | Gln | Gly | Met | Lys | Lys | Leu | Ser | Tyr | Ile | Arg | Ile | Ala | |
| | | | 180 | | | | 185 | | | | | 190 | | | | |

| GAT | ACC | AAT | ATC | ACC | AGC | ATT | CCT | CAA | GGT | CTT | CCT | CCT | TCC | CTT | ACG | 624 |
| Asp | Thr | Asn | Ile | Thr | Ser | Ile | Pro | Gln | Gly | Leu | Pro | Pro | Ser | Leu | Thr | |
| | | 195 | | | | 200 | | | | | 205 | | | | | |

| GAA | TTA | CAT | CTT | GAT | GGC | AAC | AAA | ATC | AGC | AGA | GTT | GAT | GCA | GCT | AGC | 672 |
| Glu | Leu | His | Leu | Asp | Gly | Asn | Lys | Ile | Ser | Arg | Val | Asp | Ala | Ala | Ser | |
| | 210 | | | | | 215 | | | | | 220 | | | | | |

| CTG | AAA | GGA | CTG | AAT | AAT | TTG | GCT | AAG | TTG | GGA | TTG | AGT | TTC | AAC | AGC | 720 |
| Leu | Lys | Gly | Leu | Asn | Asn | Leu | Ala | Lys | Leu | Gly | Leu | Ser | Phe | Asn | Ser | |
| 225 | | | | | 230 | | | | | 235 | | | | | 240 | |

| ATC | TCT | GCT | GTT | GAC | AAT | GGC | TCT | CTG | GCC | AAC | ACG | CCT | CAT | CTG | AGG | 768 |
| Ile | Ser | Ala | Val | Asp | Asn | Gly | Ser | Leu | Ala | Asn | Thr | Pro | His | Leu | Arg | |
| | | | | 245 | | | | | 250 | | | | | 255 | | |

| GAG | CTT | CAC | TTG | GAC | AAC | AAC | AAG | CTT | ACC | AGA | GTA | CCT | GGT | GGG | CTG | 816 |
| Glu | Leu | His | Leu | Asp | Asn | Asn | Lys | Leu | Thr | Arg | Val | Pro | Gly | Gly | Leu | |
| | | | 260 | | | | 265 | | | | | 270 | | | | |

```
GCA  GAG  CAT  AAG  TAC  ATC  CAG  GTT  GTC  TAC  CTT  CAT  AAC  AAC  AAT  ATC           864
Ala  Glu  His  Lys  Tyr  Ile  Gln  Val  Val  Tyr  Leu  His  Asn  Asn  Asn  Ile
          275                     280                         285

TCT  GTA  GTT  GGA  TCA  AGT  GAC  TTC  TGC  CCA  CCT  GGA  CAC  AAC  ACC  AAA           912
Ser  Val  Val  Gly  Ser  Ser  Asp  Phe  Cys  Pro  Pro  Gly  His  Asn  Thr  Lys
          290                     295                         300

AAG  GCT  TCT  TAT  TCG  GGT  GTG  AGT  CTT  TTC  AGC  AAC  CCG  GTC  CAG  TAC           960
Lys  Ala  Ser  Tyr  Ser  Gly  Val  Ser  Leu  Phe  Ser  Asn  Pro  Val  Gln  Tyr
305                           310                      315                      320

TGG  GAG  ATA  CAG  CCA  TCC  ACC  TTC  AGA  TGT  GTC  TAC  GTG  CGC  TCT  GCC          1008
Trp  Glu  Ile  Gln  Pro  Ser  Thr  Phe  Arg  Cys  Val  Tyr  Val  Arg  Ser  Ala
                    325                     330                      335

ATT  CAA  CTC  GGA  AAC  TAT                                                            1026
Ile  Gln  Leu  Gly  Asn  Tyr
                    340
```

( 2 ) INFORMATION FOR SEQ ID NO:2:

( i ) SEQUENCE CHARACTERISTICS:
        ( A ) LENGTH: 342 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gly  Pro  Phe  Gln  Gln  Arg  Gly  Leu  Phe  Asp  Phe  Met  Leu  Glu  Asp  Glu
 1                   5                        10                       15

Ala  Ser  Gly  Ile  Gly  Pro  Glu  Val  Pro  Asp  Asp  Arg  Asp  Phe  Glu  Pro
               20                       25                       30

Ser  Leu  Gly  Pro  Val  Cys  Pro  Phe  Arg  Cys  Gln  Cys  His  Leu  Arg  Val
          35                        40                       45

Val  Gln  Cys  Ser  Asp  Leu  Gly  Leu  Asp  Lys  Val  Pro  Lys  Asp  Leu  Pro
     50                        55                       60

Pro  Asp  Thr  Thr  Leu  Leu  Asp  Leu  Gln  Asn  Asn  Lys  Ile  Thr  Glu  Ile
 65                       70                       75                       80

Lys  Asp  Gly  Asp  Phe  Lys  Asn  Leu  Lys  Asn  Leu  His  Ala  Leu  Ile  Leu
                    85                       90                       95

Val  Asn  Asn  Lys  Ile  Ser  Lys  Val  Ser  Pro  Gly  Ala  Phe  Thr  Pro  Leu
               100                      105                      110

Val  Lys  Leu  Glu  Arg  Leu  Tyr  Leu  Ser  Lys  Asn  Gln  Leu  Lys  Glu  Leu
          115                      120                      125

Pro  Glu  Lys  Met  Pro  Lys  Thr  Leu  Gln  Glu  Leu  Arg  Ala  His  Glu  Asn
     130                      135                      140

Glu  Ile  Thr  Lys  Val  Arg  Lys  Val  Thr  Phe  Asn  Gly  Leu  Asn  Gln  Met
145                      150                      155                      160

Ile  Val  Ile  Glu  Leu  Gly  Thr  Asn  Pro  Leu  Lys  Ser  Ser  Gly  Ile  Glu
                    165                      170                      175

Asn  Gly  Ala  Phe  Gln  Gly  Met  Lys  Lys  Leu  Ser  Tyr  Ile  Arg  Ile  Ala
               180                      185                      190

Asp  Thr  Asn  Ile  Thr  Ser  Ile  Pro  Gln  Gly  Leu  Pro  Pro  Ser  Leu  Thr
          195                      200                      205

Glu  Leu  His  Leu  Asp  Gly  Asn  Lys  Ile  Ser  Arg  Val  Asp  Ala  Ala  Ser
     210                      215                      220

Leu  Lys  Gly  Leu  Asn  Asn  Leu  Ala  Lys  Leu  Gly  Leu  Ser  Phe  Asn  Ser
225                      230                      235                      240

Ile  Ser  Ala  Val  Asp  Asn  Gly  Ser  Leu  Ala  Asn  Thr  Pro  His  Leu  Arg
                    245                      250                      255
```

-continued

| | | | | | | | | | | | | | | |
|---|---|---|---|---|---|---|---|---|---|---|---|---|---|---|
| Glu | Leu | His | Leu 260 | Asp | Asn | Asn | Lys | Leu 265 | Thr | Arg | Val | Pro | Gly 270 | Gly | Leu |
| Ala | Glu | His 275 | Lys | Tyr | Ile | Gln | Val 280 | Val | Tyr | Leu | His | Asn 285 | Asn | Asn | Ile |
| Ser | Val 290 | Val | Gly | Ser | Ser | Asp 295 | Phe | Cys | Pro | Pro | Gly 300 | His | Asn | Thr | Lys |
| Lys 305 | Ala | Ser | Tyr | Ser | Gly 310 | Val | Ser | Leu | Phe | Ser 315 | Asn | Pro | Val | Gln | Tyr 320 |
| Trp | Glu | Ile | Gln | Pro 325 | Ser | Thr | Phe | Arg | Cys 330 | Val | Tyr | Val | Arg | Ser 335 | Ala |
| Ile | Gln | Leu | Gly 340 | Asn | Tyr | | | | | | | | | | |